United States Patent
Jiang

(12) 
(10) Patent No.: US 12,402,794 B2
(45) Date of Patent: Sep. 2, 2025

(54) PHOTOACOUSTIC IMAGING DEVICE AND LIGHT-TRANSMISSIBLE ULTRASONIC TRANSDUCER THEREOF

(71) Applicant: QISDA CORPORATION, Taoyuan (TW)

(72) Inventor: Fu-Sheng Jiang, Taoyuan (TW)

(73) Assignee: Qisda Corporation, Taoyuan (TW)

( * ) Notice: Subject to any disclaimer, the term of this patent is extended or adjusted under 35 U.S.C. 154(b) by 219 days.

(21) Appl. No.: 18/121,593

(22) Filed: Mar. 15, 2023

(65) Prior Publication Data

US 2024/0016389 A1 Jan. 18, 2024

(30) Foreign Application Priority Data

Jul. 13, 2022 (TW) .................................. 111126301

(51) Int. Cl.
*A61B 5/00* (2006.01)
*A61B 8/00* (2006.01)

(52) U.S. Cl.
CPC .............. *A61B 5/0095* (2013.01); *A61B 8/44* (2013.01)

(58) Field of Classification Search
CPC .................................................... A61B 5/0095
See application file for complete search history.

(56) References Cited

U.S. PATENT DOCUMENTS

2007/0164632 A1* 7/2007 Adachi .............. G01N 29/2437
310/311
2011/0066023 A1* 3/2011 Kanayama ......... G01N 29/0609
600/407
2013/0042688 A1* 2/2013 Luo .................... G01N 21/1702
73/606
2014/0018660 A1* 1/2014 Wada .................... B06B 1/0607
600/407
2023/0042741 A1* 2/2023 Rohling ............. G01N 29/2406

FOREIGN PATENT DOCUMENTS

TW 201310018 A1 3/2013
TW 201413548 A 4/2014

OTHER PUBLICATIONS

Y. Qiu et al, "Piezoelectric Micromachined Ultrasound Transducer (PMUT) Arrays for Integrated Sensing, Actuation and Imaging", Sensors, vol. 15, pp. 8020-8041, Apr. 2015 (Year: 2015).*

* cited by examiner

*Primary Examiner* — Jeffrey G Hoekstra
*Assistant Examiner* — Nyrobi Celestine

(57) ABSTRACT

A photoacoustic imaging device is suitable for performing photoacoustic imaging on an object to be tested and includes a light emitting device and a light-transmissible ultrasonic transducer. The light emitting device emits a beam along an optical axis. The light-transmissible ultrasonic transducer is disposed on the light emitting device at the optical axis and includes a transparent substrate and a plurality of ultrasonic transducer units. The plurality of ultrasonic transducer units is disposed on the transparent substrate and allows the beam to pass therethrough and be incident to the object to be tested along the optical axis, for coaxially receiving an ultrasound transmitted from the object to be tested along the optical axis after the beam is incident into the object to be tested.

18 Claims, 3 Drawing Sheets

PHOTOACOUSTIC IMAGING DEVICE AND LIGHT-TRANSMISSIBLE ULTRASONIC TRANSDUCER THEREOF

BACKGROUND OF THE INVENTION

1. Field of the Invention

The present invention relates to a photoacoustic imaging device and a light-transmissible ultrasonic transducer thereof, and more specifically, to a photoacoustic imaging device directly disposing a transparent substrate having ultrasonic transducer units at an optical axis of a light emitting device for allowing the ultrasonic transducer units to coaxially receive an ultrasound transmitted from an object to be tested and a light-transmissible ultrasonic transducer thereof.

2. Description of the Prior Art

With rapid development of medical testing technology, a photoacoustic imaging method for forming images by the photoacoustic effect has been widely applied to non-invasive medical testing. The photoacoustic imaging principle is that an object to be tested (e.g., hemoglobin in red blood cells) will convert part of beam energy into an ultrasound when a light source (e.g., a laser light source) emits a beam to the object to be tested. At this time, the ultrasound transmitted from the object to be tested will be received and then analyzed by an ultrasonic transducer to generate a two-dimensional or three-dimensional image corresponding to the object to be tested for subsequent medical testing and diagnosis. However, since the ultrasonic transducer is opaque, it can only adopt the dislocation design in which the light source and the ultrasonic transducer are disposed in a non-coaxial arrangement. For example, a testing probe could have a light exit opening to allow the beam to pass therethrough, and the ultrasonic transducer could be disposed around the light exit opening for non-coaxially receiving the ultrasound transmitted from the object to be tested. In such a manner, it may cause a poor photoacoustic-signal receiving efficiency and an image distortion problem.

SUMMARY OF THE INVENTION

The present invention provides a photoacoustic imaging device suitable for performing photoacoustic imaging on an object to be tested. The photoacoustic imaging device includes a light emitting device and a light-transmissible ultrasonic transducer. The light emitting device emits a beam along an optical axis. The light-transmissible ultrasonic transducer is disposed on the light emitting device at the optical axis. The light-transmissible ultrasonic transducer includes a transparent substrate and a plurality of ultrasonic transducer units. The plurality of ultrasonic transducer units is disposed on the transparent substrate. The plurality of ultrasonic transducer units allows the beam to pass therethrough and be incident to the object to be tested along the optical axis, for coaxially receiving an ultrasound transmitted from the object to be tested along the optical axis after the beam is incident into the object to be tested.

The present invention further provides a light-transmissible ultrasonic transducer mounted on a light emitting device for performing photoacoustic imaging on an object to be tested. The light emitting device emits a beam along an optical axis. The light-transmissible ultrasonic transducer includes a transparent substrate and a plurality of ultrasonic transducer units. The transparent substrate is located on the optical axis. The plurality of ultrasonic transducer units is disposed on the transparent substrate. The plurality of ultrasonic transducer units allows the beam to pass therethrough and be incident to the object to be tested along the optical axis, for coaxially receiving an ultrasound transmitted from the object to be tested along the optical axis after the beam is incident into the object to be tested.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
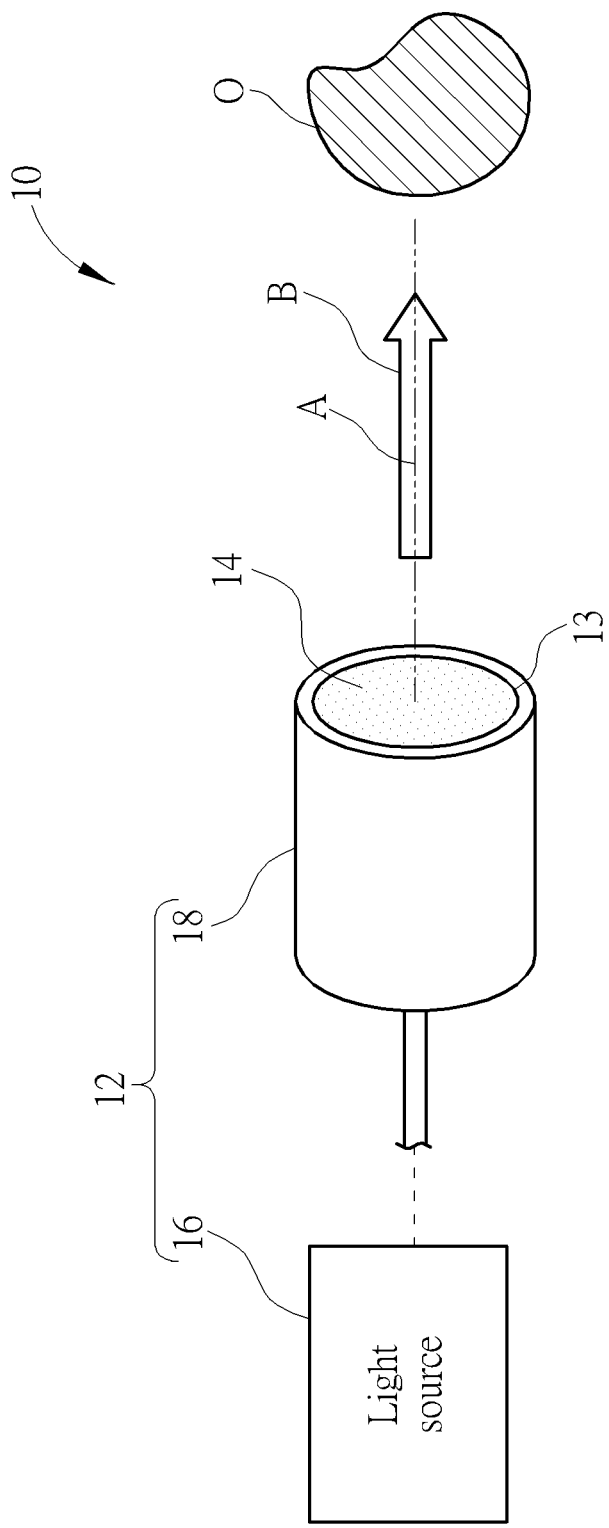
FIG. 1 is a diagram of a photoacoustic imaging device according to an embodiment of the present invention.

Please refer to FIG. 1, which is a diagram of a photoacoustic imaging device 10 according to an embodiment of the present invention. The photoacoustic imaging device 10 could be preferably suitable for performing photoacoustic imaging on an object O to be tested (could be living tissue suitable for photoacoustic imaging, such as hemoglobin in red blood cells, which is briefly depicted as an irregular block in FIG. 1). As shown in FIG. 1, the photoacoustic imaging device 10 includes a light emitting device 12 and a light-transmissible ultrasonic transducer 14. The light emitting device 12 emits a beam B along an optical axis A. To be more specific, the light emitting device 12 could have a light exit opening 13 such that the beam B can be emitted out of the light exit opening 13 along the optical axis A, and the light-transmissible ultrasonic transducer 14 and the light exit opening 13 could preferably have the same area (but not limited thereto, meaning that the photoacoustic imaging device 10 could adopt the design that the area of the light-transmissible ultrasonic transducer 14 is larger or smaller than the area of the light exit opening 13). In this embodiment, as shown in FIG. 1, the light emitting device 12 could include a light source 16 (briefly depicted as a functional block in FIG. 1) and an optical fiber probe 18. The light source 16 could be preferably a laser light source for emitting the beam B, but the present invention is not limited thereto, meaning that the light source 16 could be other light source device commonly applied to photoacoustic imaging, such as an LED (Light Emitting Diode) light source. The optical fiber probe 18 is connected to the light source 16 to guide the beam B to be emitted out of the light exit opening 13 along the optical axis A via the total internal reflection characteristics in a fiber tube of the optical fiber probe 18, so as to reduce the light loss of the beam B and improve the light usage efficiency of the beam B. To be noted, the light source design of the photoacoustic imaging device 10 is not limited to the aforesaid probe design in this embodiment. For example, in another embodiment, the photoacoustic imaging device 10 could adopt the design that the light emitting device is a laser light source or an LED light source and directly emits the beam B to the light-transmissible ultrasonic transducer 14 in a rear projection manner.

Figure 2:
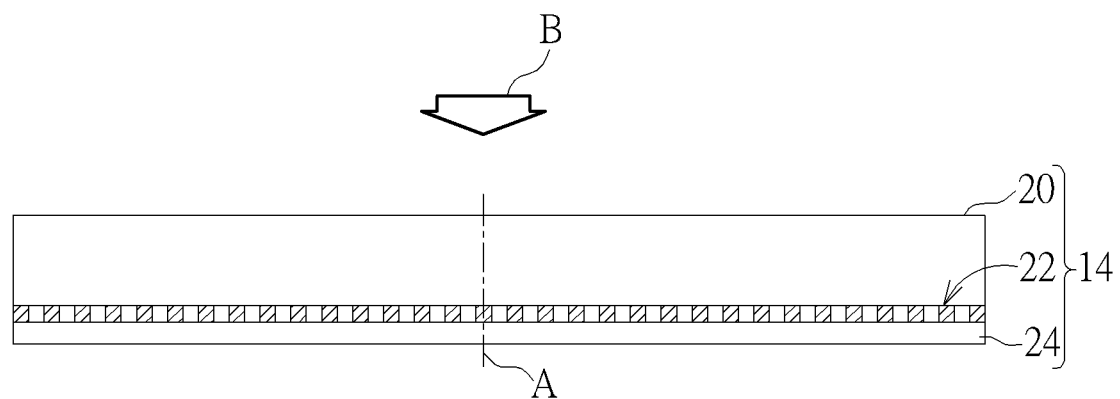
FIG. 2 is a cross-sectional diagram of a light-transmissible ultrasonic transducer in FIG. 1.
Figure 3:
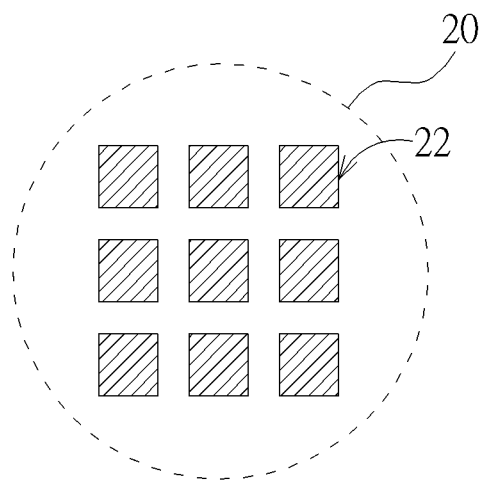
FIG. 3 is an enlarged diagram showing arrangement of ultrasonic transducer units in FIG. 2 on a transparent substrate.

Please refer to FIG. 1 and FIG. 2. FIG. 2 is a cross-sectional diagram of the light-transmissible ultrasonic transducer 14 in FIG. 1. As shown in FIG. 1 and FIG. 2, the light-transmissible ultrasonic transducer 14 is disposed on the light emitting device 12 at the optical axis A and includes a transparent substrate 20 and a plurality of ultrasonic transducer units 22. The transparent substrate 20 could be made of transparent material (e.g., glass) or translucent material (e.g., plastic) to generate the light transmission effect. The plurality of ultrasonic transducer units 22 is disposed on the transparent substrate 20 and allows the beam B to pass therethrough and be incident to the object O to be tested along the optical axis A, for coaxially receiving an ultrasound transmitted from the object to be tested along the optical axis A after the beam B is incident into the object O to be tested. The plurality of ultrasonic transducer units 22 could be preferably disposed on the transparent substrate in a matrix arrangement (as shown in FIG. 3, wherein the amount of the ultrasonic transducer unit 22 is not limited thereto) for performing two-dimensional measurement on the object O to be tested, but the present invention is not limited thereto. For example, in another embodiment, the light-transmissible ultrasonic transducer 14 could adopt the design that the plurality of ultrasonic transducer units 22 could be preferably disposed on the transparent substrate in a linear arrangement for performing one-dimensional measurement on the object O to be tested. As for which arrangement is adopted, it depends on the practical medical testing application of the photoacoustic imaging device 10. Furthermore, as shown in FIG. 2, the light-transmissible ultrasonic transducer 14 could further include a transparent protection film 24. The transparent protection film 24 could be made of transparent or translucent film material (e.g., silicon dioxide) and cover the plurality of ultrasonic transducer units 22 for simultaneously providing the protection and light transmission effects.

Figure 4:
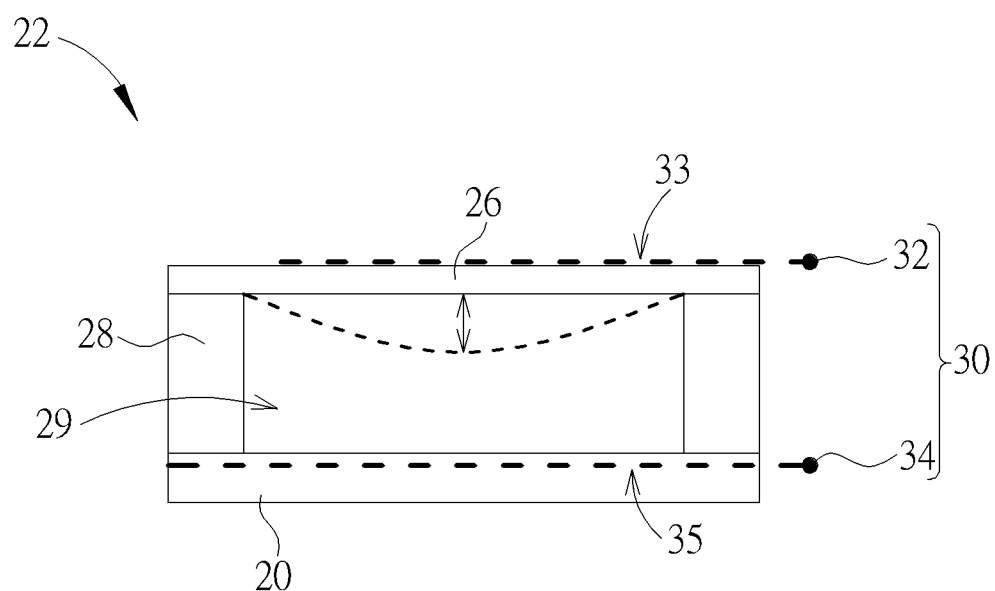
FIG. 4 is a cross-sectional diagram of the ultrasonic transducer unit in FIG. 3.

More detailed description for the ultrasonic transducer unit 22 is provided as follows. Please refer to FIG. 4, which is a cross-sectional diagram of the ultrasonic transducer unit 22 in FIG. 3. As shown in FIG. 4, each ultrasonic transducer unit 22 could include a transparent film 26 (e.g., a silicon-dioxide film, but not limited thereto), an insulation support layer 28, and a transparent electrode layer 30. Each ultrasonic transducer unit 22 could be preferably a CMUT (Capacitive Micromachined Ultrasonic Transducer), but not limited thereto, meaning that each ultrasonic transducer unit 22 could be other type of micromachined ultrasonic transducer, such as a PMUT (Piezoelectric Micromachined Ultrasonic Transducer). The insulation support layer 28 is connected to the transparent film 26 and the transparent substrate 20 for forming a cavity 29 cooperatively with the transparent film 26 and the transparent substrate 20, and the transparent electrode layer 30 is electrically connected to the transparent film 26. To be more specific, in this embodiment, the transparent electrode layer 30 could adopt the circuit gap design (but not limited thereto, meaning that the present invention could adopt the transparent electrode design that the transparent electrode layer 30 is formed on the transparent film 26 and is made of ITO (Indium Tin Oxide) material in another embodiment). For example, as shown in FIG. 4, the transparent electrode layer 30 could include a first circuit layer 32 and a second circuit layer 34. The first circuit layer 32 is formed on the transparent film 26 and has at least one first circuit gap 33, and the second circuit layer 34 is formed on the transparent substrate 20 and has at least one second circuit gap 35. Accordingly, when the beam B is incident to the ultrasonic transducer unit 22, the beam B can pass through the transparent substrate 20, the second circuit gap 35, the cavity 29, the transparent film 26, and the first circuit gap 33 to be incident to the object O to be tested along the optical axis A.

Via the aforesaid design, when the light source 16 emits the beam B, the beam B can pass through the ultrasonic transducer units 22 via optical guidance of the optical fiber probe 18 to be emitted out of the light exit opening 13, so as to be incident to the object O to be tested along the optical axis A. At this time, as known from the aforesaid photoacoustic imaging principle, the object O to be tested can convert the beam B into an ultrasound, so that the transparent film 26 of each ultrasonic transducer unit 22 can vibrate up and down relative to the cavity 29 when the transparent film 26 coaxially receives the ultrasound transmitted from the object O to be tested along the optical axis A. In such a manner, the transparent electrode layer 30 can generate an electronic signal corresponding to the ultrasound according to vibration of the transparent film 26, and the photoacoustic imaging device 10 can analyze the electronic signal to generate a two-dimensional or three-dimensional image corresponding to the object O to be tested for subsequent medical testing and diagnosis.

In summary, compared with the prior art adopting the dislocation design in which the light source and the ultrasonic transducer are disposed in a non-coaxial arrangement, the present invention adopts the coaxial arrangement design in which the transparent substrate having the light-transmissible ultrasonic transducer units is directly disposed at the optical axis of the light emitting device to generate the effect that the light-transmissible ultrasonic transducer units can coaxially receive the ultrasound transmitted from the object to be tested. Thus, the present invention can efficiently solve the poor photoacoustic-signal receiving efficiency and image distortion problems aforementioned in the prior art, so as to greatly improve the image forming quality and measurement accuracy of the photoacoustic imaging device.

It should be mentioned that the transparent design adopted by the photoacoustic imaging device is not limited to the design in which the ultrasonic transducer units are light-transmissible. For example, the present invention could adopt the design in which there is a gap formed between two adjacent ultrasonic transducer units for allowing the beam to pass therethrough. That is, in another embodiment, each ultrasonic transducer unit could be a common ultrasonic transducer device, such as a CMUT, a PMUT, or a piezoelectric transducer, and any two adjacent ultrasonic transducer units on the transparent substrate are spaced away from each other by a gap to allow the beam to pass therethrough (e.g., the design that a gap between any two adjacent ultrasonic transducer units 22 as shown in FIG. 3 is further increased to allow the beam B to pass therethrough), so as to generate the effect that the ultrasonic transducer device is light-transmissible. As for other related description for this embodiment, it could be reasoned by analogy according to the aforesaid embodiment and omitted herein.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A photoacoustic imaging device suitable for performing photoacoustic imaging on an object to be tested, the photoacoustic imaging device comprising:
    a light emitting device emitting a beam along an optical axis; and
    a light-transmissible ultrasonic transducer disposed on the light emitting device at the optical axis, the light-transmissible ultrasonic transducer comprising:
        a transparent substrate; and
        a plurality of ultrasonic transducer units disposed on the transparent substrate each ultrasonic transducer unit comprising:
            a transparent film forming a cavity together with the transparent substrate; and
            a transparent electrode layer comprising a first circuit layer and a second circuit layer, the first circuit layer being formed on the transparent film and having a first circuit gap, and the second circuit layer being formed on the transparent substrate and having a second circuit gap;
    wherein when the beam is incident to the plurality of ultrasonic transducer units, the beam passes through the transparent substrate, the second circuit gap, the cavity, the transparent film and the first circuit gap sequentially along the optical axis and then is incident to the object to be tested and the plurality of ultrasonic transducer units coaxially receives an ultrasound transmitted from the object to be tested after the beam is incident into the object to be tested.

2. The photoacoustic imaging device of claim 1, wherein the light emitting device has a light exit opening to allow the beam to be emitted out of the light exit opening, and the light-transmissible ultrasonic transducer and the light exit opening have the same area.

3. The photoacoustic imaging device of claim 1, wherein the light emitting device comprises:
    a light source emitting the beam; and
    an optical fiber probe connected to the light source to guide the beam to be emitted along the optical axis.

4. The photoacoustic imaging device of claim 3, wherein the light source is a laser light source or an LED (Light Emitting Diode) light source.

5. The photoacoustic imaging device of claim 1, wherein the light emitting device is a laser light source or an LED light source.

6. The photoacoustic imaging device of claim 1, wherein the plurality of ultrasonic transducer units is disposed on the transparent substrate in a linear arrangement to perform one-dimensional measurement on the object to be tested, or is disposed on the transparent substrate in a matrix arrangement to perform two-dimensional measurement on the object to be tested.

7. The photoacoustic imaging device of claim 1, wherein any two adjacent ultrasonic transducer units are spaced away from each other by a gap and the beam passes through the gap along the optical axis and is incident to the object to be tested.

8. The photoacoustic imaging device of claim 1, wherein each ultrasonic transducer unit is a CMUT (Capacitive Micromachined Ultrasonic Transducer), a PMUT (Piezoelectric Micromachined Ultrasonic Transducer), or a piezoelectric transducer.

9. The photoacoustic imaging device of claim 1, wherein each ultrasonic transducer unit further comprises:
    an insulation support layer connected to the transparent film and the transparent substrate to form the cavity cooperatively with the transparent film and the transparent substrate for allowing the transparent film to vibrate up and down relative to the cavity when the transparent film receives the ultrasound.

10. The photoacoustic imaging device of claim 9, wherein the transparent electrode layer is formed on the transparent film and is made of ITO (Indium Tin Oxide) material.

11. The photoacoustic imaging device of claim 1, wherein the light-transmissible ultrasonic transducer further comprises:
    a transparent protection film covering the plurality of ultrasonic transducer units.

12. A light-transmissible ultrasonic transducer mounted on a light emitting device for performing photoacoustic imaging on an object to be tested, the light emitting device emitting a beam along an optical axis, the light-transmissible ultrasonic transducer comprising:
    a transparent substrate located on the optical axis; and
    a plurality of ultrasonic transducer units disposed on the transparent substrate, each ultrasonic transducer unit comprising:
        a transparent film forming a cavity together with the transparent substrate; and
        a transparent electrode layer comprising a first circuit layer and a second circuit layer, the first circuit layer being formed on the transparent film and having a first circuit gap, and the second circuit layer being formed on the transparent substrate and having a second circuit gap;
    wherein when the beam is incident to the plurality of ultrasonic transducer units, the beam passes through the transparent substrate, the second circuit gap, the cavity, the transparent film and the first circuit gap sequentially along the optical axis and then is incident to the object to be tested, and the plurality of ultrasonic transducer units coaxially receives an ultrasound transmitted from the object to be tested after the beam is incident into the object to be tested.

13. The light-transmissible ultrasonic transducer of claim 12, wherein the light emitting device has a light exit opening to allow the beam to be emitted out of the light exit opening, and the light-transmissible ultrasonic transducer and the light exit opening have the same area.

14. The light-transmissible ultrasonic transducer of claim 12, wherein the plurality of ultrasonic transducer units is disposed on the transparent substrate in a linear arrangement to perform one-dimensional measurement on the object to be tested, or is disposed on the transparent substrate in a matrix arrangement to perform two-dimensional measurement on the object to be tested.

15. The light-transmissible ultrasonic transducer of claim 12, wherein any two adjacent ultrasonic transducer units are spaced away from each other by a gap and the beam passes through the gap along the optical axis and is incident to the object to be tested.

16. The light-transmissible ultrasonic transducer of claim 15, wherein each ultrasonic transducer unit is a CMUT, a PMUT, or a piezoelectric transducer.

17. The light-transmissible ultrasonic transducer of claim 12, wherein each ultrasonic transducer unit comprises:
    an insulation support layer connected to the transparent film and the transparent substrate to form the cavity cooperatively with the transparent film and the transparent substrate for allowing the transparent film to vibrate up and down relative to the cavity when the transparent film receives the ultrasound.

18. The light-transmissible ultrasonic transducer of claim 17, wherein the transparent electrode layer is formed on the transparent film and is made of ITO material.

\* \* \* \* \*